United States Patent [19]

Hayashi

[11] 4,094,671

[45] June 13, 1978

[54] GOLD COLOR COPPER ALLOY FOR RESTORATIVE DENTISTRY

[76] Inventor: Osamu Hayashi, No. 26-6, Okusawa 2-chome, Setagaya-ku, Tokyo-to, Japan

[21] Appl. No.: 704,553

[22] Filed: Jul. 12, 1976

[30] Foreign Application Priority Data

May 7, 1976 Japan .................................. 51-51851

[51] Int. Cl.² .......................... A61C 13/00; C22C 9/04
[52] U.S. Cl. .......................................... 75/157.5; 32/5; 32/8; 32/12; 32/15; 75/134 B; 75/134 C; 75/178 C
[58] Field of Search ............. 75/134 C, 134 B, 157.5, 75/178 C; 32/5, 6, 8, 15, 12

[56] References Cited

U.S. PATENT DOCUMENTS

| 1,907,219 | 5/1933 | Sieg ..................................... 75/157.5 |
| 2,035,423 | 3/1936 | Bunn .................................... 75/157.5 |
| 2,235,634 | 3/1941 | Hensel et al. ................... 75/157.5 X |
| 2,296,706 | 9/1942 | Corson ............................... 75/157.5 |
| 3,977,869 | 8/1976 | Steine et al. ................... 75/157.5 X |

FOREIGN PATENT DOCUMENTS

378,133  7/1964  Switzerland ...................... 75/157.5

*Primary Examiner*—C. Lovell
*Attorney, Agent, or Firm*—Steinberg & Blake

[57] ABSTRACT

A copper alloy having a gold color and being particularly suitable for restorative dentistry and consisting essentially of copper, zinc and a small amount of zirconium. Other additions may be included in the alloy.

7 Claims, No Drawings

GOLD COLOR COPPER ALLOY FOR RESTORATIVE DENTISTRY

BACKGROUND OF THE INVENTION

Severe restrictions are placed on the alloys which are used for restorative dentistry because of the particular requirements of such alloys with respect to various properties thereof which are essential for the particular use to which the alloys are put. In general, the alloys which have conventionally been found to be most suitable are gold alloys or platinum-containing gold alloys of high quality. These alloys have been most used not only because of the traditional preference of the gold color but also because the gold has extremely high chemical stability against discoloration and dissolution in the mouth as well as having various preferred mechanical properties such as high extensibility, high workability and high wear resistance. However, while gold has been found to be most suitable, the price is extremely high and various substitutes have been sought.

Among the alloy substitutes for gold, the alloys containing copper as a principal ingredient and having a gold color have been considered and researched with respect to the desire of obtaining those properties of the alloys which are as similar as possible to the properties of the gold alloys.

These substitute alloys which are used for restorative dentistry are generally used in forms such as inlay, a crown, a clasp and a bridge, and the clinical value thereof depends, for example, in the case of the inlay, on the extent to which the alloy can prevent the tooth to which it becomes associated from again becoming decayed, as well as how the alloy can maintain the shape and function of the tooth. Most important, is the length of time during which the alloy can be effective for these purposes.

From the clinical standpoint, the physical properties which can protect the alloys against breakage and deformation are such wherein the tensile strength is greater than 40kg/mm$^2$, an extensibility greater than 10% and a hardness greater than 180 (Vickers hardness units). These are considered the optimum characteristics, however, the high degree of hardness is actually too high and is rather inconvenient in practice.

Furthermore, a conflicting relationship exists between the tensile strength and the extensibility, and the difficulty in manufacturing of the alloys for restorative dentistry is to a great extent caused by the need to balance each of these properties with the other. The advantage of the high quality gold alloys, as previously mentioned, exists in this respect, i.e. in the fact that the tensile strength and extensibility which are actually in conflict with each other are mutually balanced in the case of the high quality gold alloys while presenting sufficiently high values to provide satisfactory properties.

There have been considerable difficulties in providing substitute alloys which meet this requirement. Although the gold-silver-palladium alloys exhibit properties similar to those of the gold alloys, the problem with these gold-silver-palladium alloys is that the same also exhibit melting points which are unsuitably high for casting. In addition, these alloys are also relatively high in price.

On the other hand, various copper alloys containing copper as the principal ingredient and also exhibiting a gold color have been prooposed and considerable research has been conducted to obtain properties thereof which are as similar as possible to the optimum properties.

One of these gold color copper alloys, referred to as "Neoden" exhibits many of the preferred properties. Neoden consists, by weight, of 51% of copper, 47% of zinc, 1.0% of indium, 0.2% of tellurium and 0.8% of silicon, melted together into an alloy which is claimed to be as good as 14K gold alloy. Also, compared to the 14K gold alloy with silver, which has principally been used only for relatively simple inlays because of the hardness and elasticity thereof, Neoden is also claimed to be useful as an inlay for relatively complicated decayed cavities and also for crowns and bridges of high adaptability. In addition to this wide range of application, Neoden is also of course claimed to be advantageous from the standpoint of economy since the material price thereof is approximately 1/6 the price of 14K gold alloy approximately 1/6 the price of gold-palladium alloy.

Another gold color copper alloy which has been developed particularly because of the color tone thereof consists by weight of 47 to 85% of copper, 10 to 50% of zinc plus 0.3–15% of indium, 0.02 to 3% of tellurium and 0.2 to 3% of silicon. This alloy has also been used for restorative dentistry and is as good as Neoden with respect to extensibility, adaptability for casting and workability. This gold color copper alloy has a high elasticity and has accordingly found to be suitable especially for use as a cast spring and as a one piece cast for restorative dentistry. However, it has not been found suitable for other applications.

Until the present, Neoden has been considered to be the most preferred gold color copper alloy in view of the versatility thereof, the tensile strength and the extensibility. However, Neoden has encountered a very serious problem, particularly with respect to the tendency thereof to discoloration, a low corrosion resistance and consequently a tendency to breakage or damage due to corrosion. Also, with respect to hardness, Neoden is slightly too hard to be easily worked and is inferior to the gold alloys. Furthermore, during casting the formation of air bubbles often occurs and this is also a problem in the manufacturing of the alloys. Of the various disadvantages, the tendency to discoloration is the most serious from the aesthetic viewpoint and considerably lowers the value of the alloy from the commercial standpoint. Experiments have shown that although it might be possible to obtain products of satisfactory quality free from discoloration when producing the alloy on a laboratory scale from materials totalling approximately 200g in weight, the products obtained in mass scale from the materials of 1kg or more exhibit a tendency to darkening once the product has been utilized as an inlay, for example, in a decayed cavity of the tooth. This fact has posed a problem for the maintenance of quality in mass production and severely restricted the use of Neoden commercially.

SUMMARY OF THE INVENTION

Generally speaking, in accordance with the present invention, a gold color copper alloy is provided consisting essentially, by weight, of 48–52% of copper, 47–51% of zinc and 0.1–1.0% of zirconium. Additionally, if desired, this alloy of the present invention may also include, by weight ratio relative to the entire quantity of the alloy, one or more of the following: less than 1.2% of nickel, less than 1.0% of indium, less than 1.0% of silicon, less than 0.5% of beryllium and less than 0.5% of lithium.

Accordingly, it is an object of this invention to provide gold color copper alloys presenting all of the best characteristics of gold alloys while providing the economy of copper alloys.

It is a further object of the present invention to provide copper alloys which are suitable for casting for use in connection with restorative dentistry, which alloys are free of rare metals.

It is still another object of the present invention to provide gold color copper alloys having a sufficiently high elasticity to be useful not only in the form of an inlay and a crown, but which are also useful in the form of bridges or clasps.

It is yet a further object of the present invention to provide gold color copper alloys having a melting point as low as 950° C and also being free from discoloration while exhibiting a color tone equivalent to true gold alloys.

The present invention further comprises as an object thereof the provision of gold color copper alloys of high tensile strength and high extensibility with these values being well balanced with respect to each other.

Other objects and advantages of the present invention will be apparent from a further reading of the specification and of the appended claims.

In seeking to achieve all of these objects, as well as in seeking to overcome the quality variation during alloying on a mass scale, I have prepared trial alloys of more than 10,000 types with the addition of various metallic elements to arrive at the alloy compositions which provide all of the requirements which render the same most suitable for use in restorative dentistry. Thus, in developing the gold color copper alloys of the present invention, the following desiderata were aimed at:

1. The provision of a gold color copper alloy suitable for casting and containing no rare metal and consisting essentially of copper and zinc.
2. The provision of a gold color copper alloy having a high elasticity so as to render the same useful not only in the form of an inlay and crown, which are usually of relatively small size, but also in the form of a bridge or clasp.
3. The provision of an alloy having a melting point as low as 950° C or lower so that the same can be easily melted and cast utilizing an ordinary Bunsen burner or the like.
4. The provision of a gold color copper alloy having a color tone equivalent to the true gold alloys while being free from discoloration when used in the mouth.
5. The provision of the alloy having a high tensile strength and high degree of extensibility, these characteristics being balanced with respect to each other.

The gold color copper alloys of the present invention are clearly distinguished from similar alloys of the prior art in utilizing copper and zinc in weight ratios closely approximating each other and together totalling at least 95% of the entire alloy, while utilizing zirconium as an alloying metal therewith. Zirconium has never been utilized in dental alloys of this type prior to the present invention.

The use of copper and zinc in substantially equal quantities, although there is a slight difference between the quantities of each, is based upon the following knowledge: it has usually been necessary to repeat the operations of melting several times in the manufacture of alloys and this results in a variation in the tensile strength as well as in the hardness, which in general leads to deterioration. It is well known that in the process of manufacturing alloys of copper and zinc, the gold color becomes more and more reddish and the melting point rises as the quantity of copper increases with respect to the quantity of the zinc, while the gold color becomes more and more pale and the hardness increases as the quantity of zinc increases relative to the quantity of the copper. It has further been found that repeated melting rapidly reduces the tensile strength as well as the hardness through the phonemenon of dezincification which also adversely influences the color tone.

In the process of manufacturing the alloy which comprises, in addition to copper and zinc, one or more of the other metallic alloying elements previously mentioned, the operation of melting has generally been repeated two or more times, and usually three times.

Giving this aspect full consideration, I carried out an experiment with respect to alloys consisting of copper and zinc, without the addition of any other alloying elements, during which the melting operation was repeated with different ratios of the respective ingredients. These experiments showed variable measurements of tensile strength and hardness as indicated in the following table:

| Material composition | | The number of times melting and casting were repeated | | | |
|---|---|---|---|---|---|
| | | 1 | 2 | 3 | 4 |
| Copper | 50% | 37.2 | 38.4 | 39.1 | 37.2 |
| Zinc | 50% | (80) | (77) | (73) | (67) |
| Copper | 55% | 40.3 | 37.4 | 36.3 | 32.1 |
| Zinc | 45% | (73) | (65) | (55) | (46) |
| Copper | 60% | 32.0 | 29.2 | 28.3 | 26.7 |
| Zinc | 40% | (50) | (45) | (39) | (36) |

In the above table, the value in the upper row within each space constitutes the value in kg/mm$^2$ actually measured utilizing an Amsler tensile tester. The value in the lower row in each space, the values enclosed in brackets, constitutes the Brinelle hardness value.

The experimental values set forth in the above table indicate that not only is the tensile strength reduced as the quantity of zinc is reduced, but also the hardness is reduced, and both of these values are reduced as the number of repeated melting operations increases for the particular composition. However, utilizing the material composition set forth in the first row of values, i.e. 50% copper and 50% zinc, only the tensile strength progressively increased as the number of melting operations was repeated up to three melting operations, but the value sharply dropped for the fourth melting operation to a value substantially equal to the first measured value. This effect is probably due to the quantity of zinc being substantially reduced through four melting operations under the effect of dezincification, possibly to a copper to zinc ratio of 60:40.

In view of the fact that as previously mentioned the melting operation must be repeated two or more times during the alloying process in which the metallic ingredients other than copper and zinc are also melted together, the alloying is peferably started in accordance with the present invention with equal parts by weight of zinc and copper in order to obtain the tensile strength and hardness most suitable for dental purposes. It should be understood, however, that the starting quantity of zinc may be slightly higher than the quantity of copper when the melting operation must be repeated four times or more due to the effect of dezincification. The following description based on experimental measures confirms that the repeated operation of melting and casting affects the mechanical properties of copper alloy. Although the alloy containing zinc in a relatively higher quantity than the quantity of copper presents favorable mechanical properties for dental purposes, its corrosion resistance for these same purposes is disadvantageously reduced due to the high weight ratio of zinc. The oral cavity within which the alloy is used for restorative dentistry is always exposed to severly acidic or alkaline conditions so that the alloy containing a quantity of zinc as high as the quantity of copper has not been suitable for practical use due to the extremely poor corrosion resistance of such alloy which does not permit its use for many years without breakage or damage.

In consideration of this requirement I have carried out research as to how to improve the corrosion resistance of the alloy sufficiently to permit this alloy to be practically used while maintaining the advantageous mechanical properties resulting from the high content of zinc. This research led to the discovery that the addition of a proper quantity of zirconium to the alloy provides extremely improved corrosion resistance while maintaining sufficiently satisfactory mechanical properties. Thus, the present invention is characterized by the use of zinc as as one principal ingredient of the alloy in an amount which is as or greater than the quantity of the copper, which is the other principal ingredient of the alloy while also including the determined proper quantity of zirconium, this alloy providing the desired mechanical properties along with sufficient corrosion resistance to permit the use thereof for restorative dentistry.

Zirconium which is used according to the present invention in the alloy composition thereof has never been used for this purpose, namely in gold color copper alloys useful for restorative dentistry, and the use of the zirconium constitutes an essential feature of the present invention. The alloy for restorative dentistry containing the proper quantity of zirconium exhibits characteristics substantially different from the same alloy to which no zirconium has been added, these differences resulting in considerable improvements with respect to prevention of discoloration and with respect to corrosion resistance.

Prior to the present invention, tin or aluminum has been added to copper alloy compositions for dental useage as the most effective means of providing appropriate hardness. However, while tin contributes to the improvement in hardness, it also contributes to discoloration and simultaneously makes the alloy brittle. On the other hand, aluminum contributes to improvement in hardness along with extensibility and color tone and some reduction in corrosion resistance. However, the aluminum causes corrosion in the form of pockmarks over the surface of the alloy when the same is charged in the oral cavity. Thus, neither of these additives technically resolves the problems of prevention of discoloration and improvement of corrosion resistance without adverse influence upon various physical properties such as hardness, tensile strength and extensibility, while also providing a chemical stability. In contrast thereto, the addition of zirconium to the alloy composition of the present invention provides all of these advantages while even improving the above mentioned properties. The zirconium increases the corrosion resistance caused by the high quantity of zinc, and contributes to the improvement of the tensile strength and extensibility while providing mutual balance between these two factors.

Although the addition of zirconium affects the tensile strength and extensibility as shown by an experimental example below which will be discussed in greater detail, such variation in these properties can be limited to a negligible amount to obtain the desired tensile strength and extensibility depending upon the quantity of zirconium which is used in a relatively small amount in accordance with the present invention. Such addition of zirconium in the proper quantity not only remarkably improves the corrosion resistance but also increases the hardness of the alloy while improving the resistance thereof to acid and alkali.

The test results which will be set forth below were based upon gold color copper alloys according to the present invention of the composition indicated below, and, more specifically, were based upon experimental measurements conducted on alloys obtained through three melting operations.

EXAMPLE OF EXPERIMENT 1

Copper: 150 g and
zinc: 194 g
were melted together to obtain a copper-zinc mother alloy to which
Nickel: 2 g,
Indium: 1.9g,
Silicon: 1.4g,
Beryllium: 0.5g and
Lithium: 0.2g
were added and melted together, and this was divided in five equal parts to be used as sample mother alloys.

To these five equally divided sample mother alloys,
(1) Copper alone, 10g,
(2) An alloy comprising 10g of copper and 0.4g of zirconium,
(3) An alloy comprising 10g of copper and 0.6g of zirconium,
(4) An alloy comprising 10g of copper and 0.8g of zirconium, and
(5) An alloy comprising 10g of copper and 1.6g of zirconium
were added, respectively, to obtain alloys of five types consisting of a zirconium-free alloy, an alloy containing 0.4g of zirconium, an alloy containing 0.6g of zirconium, an alloy containing 0.8g of zirconium and an alloy containing 1.6g of zirconium. Experimental measurements were conducted on these sample alloys with respect to the hardness, the tensile strength and the extensibility. The results were as shown in the following table.

| Zirconium | Hardness (V.H.) | Tensile Strength (Kg/mm$^2$) | Extensibility (%) |
|---|---|---|---|
| Not added | 164.4 | 45.4 | 13.5 |
| 0.4g | 172.0 | 45.2 | 13.2 |
| 0.6g | 197.4 | 44.8 | 13.0 |
| 0.8g | 206.2 | 32.8 | 12.6 |
| 1.6g | 224.6 | 17.0 | 6.2 |

Data on hardness was obtained in this experiment as the average value of three measurements on five measurement spots of the respective sample pieces which had previously been formed by casting the respective sample alloys into plats and surface treating by buffing with a Vickers durometer (200g load) manufactured by Akashi.

Tensile strength data was obtained as the average value of measurements determined three times in tension tests on the respective sample pieces which had been cast by embedding the respective melts into 10 pieces of wax prototypes, each having a diameter of 1.2mm and a length of 60mm, utilizing the cristobalite embedder.

Extensibility data was obtained during each measurement of tensile strength by subjecting each sample piece held at opposite ends by a movable holder member and a stationary holder member, respectively, to a tension and by determining the displacement of the movable holder member relative to the stationary holder member. The extensibility value was represented by the ratio (%) of the displacement to the initial length between the movable holder member and the stationary holder member.

The weight of each sample alloy used in this experiment actually deviated from the weight anticipated from its material composition. Thus, the sample alloy without the addition of zirconium should have weighted 80g, that with 0.4g of zirconium should have weighed 80.4g, that with 0.6g of zirconium should have weighed 80.6g, that with 0.8g of zirconium should have weighed 80.8g and that with 1.6g of zirconium should have weighed 81.6g. However, the weighed value after completion of the alloying showed different values for the sample pieces inclusive of the material losses due to cutting waste when dividing into five equal parts as well as due to dezincification through the repeated melting operations and the zirconium ratios in the resulting alloy compositions differed somewhat with respect to the various quantities of zirconium added. This is shown in the following table:

| Total weight of material | Weighed value of alloy | Quantity of Zirconium addition | Content ratio of zirconium |
|---|---|---|---|
| 80 g | 76.34g | 0 g | 0% |
| 80.4g | 76.12g | 0.4g | 0.525% |
| 80.6g | 76.26g | 0.6g | 0.786% |
| 80.8g | 76.48g | 0.8g | 1.046% |
| 81.6g | 77.88g | 1.6g | 2.054% |

It is apparent that the differences found in the actually weighed values of the respective alloy samples has no influence upon the hardness, tensile strength and the extensibility.

It has been found from the examination based on the data as set forth above that the addition of zirconium in an amount higher than 1.0% has a tendency to unfavorably increase the hardness from the standpoint of workability and results in a sharp reduction in the tensile strength and extensibility. It will also be understood from this experiment that the zirconium is preferably added in an approximate weight ratio of 0.75% to the mother alloy. Furthermore, it was found that the addition of zirconium in an amount less than 0.1% has no actual effect on suppressing discoloration and improvement of corrosion resistance so that the proper quantity of zirconium for the purposes of the present invention is between 0.1 and 1.0% by weight of the overall alloy.

A series of experiments were conducted with respect to corrosion resistance in the manner described below and the experimental results are set forth in comparison with the above mentioned Neoden, the gold color copper alloy of the prior art compared to one embodiment of a gold color copper alloy of the present invention.

EMBODIMENT 1

Copper: 49.20%
Zinc: 47.79%
Zirconium: 0.92%
Nickel: 0.98%
Indium: 0.48%
Silicon: 0.40%
Beryllium: 0.12%
Lithium: 0.05%

The gold color copper alloy according to the present invention which was obtained by melting and alloying the above material composition was subjected together with said Neoden to predetermined discoloration and corrosion tests.

In the discoloration test, after being sufficiently polished by abrasive paper No. 600 according to R 6255 of JIS, respective sample pieces were immersed in
(i) 0.1% aqueous solution of sodium sulfide (37° C) and
(ii) saturated aqueous solution of sodium sulfide (20°).

Changes occurring on the surface of each sample piece 30 minutes after and 30 days after in the environments (i) and (ii) were observed and recorded.

In the corrosion test, sample pieces polished as in said discoloration test were immersed in
(iii) 10% acetic acid (20° C) and
(iv) 1% aqueous solution of sodium sulfide (20° C).

Changes occurring in the respective sample pieces 30 hours after, 3 days after, 300 hours after and 30 days after in the environments (iii) and (iv) were observed and recorded.

| Environment | Discoloration Test | |
|---|---|---|
| | NEODEN | Alloy of Embodiment 1 |
| 30 minutes after immersion in 0.1% sodium sulfide (37° C) | No change on immersed portion. Change was observed on out-of-solution portion. | No change on immersed portion. Change was observed on out-of-solution portion. |
| 30 days after immersion in 0.1% sodium sulfide (37° C) | Slight tarnish on immersed portion. Remarkable darkening on out-of-solution portion. | No change on immersed portion. Slight change on out-of-solution portion. |
| 30 minutes after immersion in saturated sodium sulfide (20° C) | No change on immersed portion. Change was observed on out-of-solution portion. | No change on immersed portion. Change was observed on out-of-solution portion. |
| 30 days after immersed in saturated sodium sulfide (20° C) | Tarnish on immersed portion. Remarkable darkening on out-of-solution portion. | No change on immersed portion. Slight change on out-of-solution portion. |

| Environment | Corrosion Test NEODEN | Alloy of Embodiment 1 |
| --- | --- | --- |
| 30 hours after immersion in 10% acetic acid (20° C) | No change both on immersed and out-of-solution portions. | No change both on immersed and out-of-solution portions. |
| 3 days after immersion in 10% acetic acid (20° C) | No change on alloy itself but blueing in solution itself. | No change both on alloy itself and in solution itself. |
| 300 hours after immersion in 10% acetic acid (20° C) | Slight change also on alloy itself and blueing in solution itself. | No change both on alloy itself and in solution itself. |
| 30 hours after, 3 days after and 300 hours after immersion in 1% aqueous solution of sodium sulfide (20° C) | No change. | No change. |

The actual chemical resistance of the alloy of the present invention was considered in reference to the alloy of embodiment 2 below through observation of changes occurring thereon when charged in the oral cavity in comparison with the prior art alloys without the addition of zirconium.

EMBODIMENT 2

Copper of 99.90% purity: 49.08g
Zinc of 99.90% purity: 47.68g
Nickel of 99.90% purity: 0.96g
Indium of 99.97% purity: 0.45g
Silicon of 98.00% purity: 0.45g
Beryllium of 99.50% purity: 0.18%
Lithium of 99.00% purity: 0.05g The above material composition was melted together into a copper-zinc mother alloy. To this copper-zinc mother alloy, Zirconium of 99.60% purity: 0.75g was added and melted together again to obtain the alloy according to the present invention. Pairs of palatine plates for upper and lower jaws each having surface area of approximately 10cm$^2$ were cast from this alloy according to the present invention and said copper-zinc mother alloy, then precisely weighed to obtain said palatine plates of uniform weight and worked for practical charge in the oral cavity.

When practically charged in the oral cavity, these palatine plates must be exposed to acidic and alkaline influences and subjected to a complicated environment comprising chemical and physical factors. The variation occurring in these palatine plates after being charged in the oral cavity for days is reflective principally of the chemical resistance thereof. A high chemical resistance is obviously reflected by a relatively small quantity of alloy liquation and the palatine plate sample comprising such an alloy is understood to present a high actual function inclusive of the other physical factors.

The following table indicates measurements of the weight variation occurring after use for days on the palatine plate for the lower jaw made of said copper-zinc mother alloy without addition of zirconium and the palatine plate for the upper jaw made of the alloy according to the present invention charged in the oral cavity of a subject A and on the palatine plate for the lower jaw made of the alloy according to the present invention and the palatine plate for the upper jaw made of said copper-zinc mother alloy without addition of zirconium charged in the oral cavity of another subject B. Both the alloy according to the present invention and the copper-zinc mother alloy without addition of zirconium were tested on each of said subjects A and B in order to eliminate a variation of the alloy liquation due to a possible physical constitution difference of both subjects which could occur if the alloy according to the present invention had been tested on only one of both subjects and the copper-zinc mother alloy without addition of zirconium on the other subject.

| Days elapsing | Subject | Reduction of weight (mg) | | Average of A-B (reduction/-cm$^2$ per day) | |
| --- | --- | --- | --- | --- | --- |
| | | Co-Zn mother alloy | Alloy of invention | Co-Zn mother alloy | Alloy of invention |
| 10 | A | 3.20 | 2.45 | 3.30mg | 2.58mg |
| | B | 3.40 | 2.70 | (0.033mg) | (0.025mg) |
| 20 | A | 5.40 | 4.40 | 5.70mg | 4.80mg |
| | B | 6.00 | 5.20 | (0.029mg) | (0.024mg) |
| 30 | A | 7.80 | 7.00 | 8.10mg | 7.30mg |
| | B | 8.40 | 7.60 | (0.027mg) | (0.024mg) |
| 40 | A | 11.20 | 9.20 | 11.50mg | 9.35mg |
| | B | 11.80 | 9.50 | (0.029mg) | (0.023mg) |

It was found on the basis of observations made during 40 days that on the average 0.030mg/cm$^2$ per day of liquation occurred in the case of the alloy without the addition of zirconium, while an average of 0.024mg/cm$^2$ per day of liquation occurred in the alloy containing therein 0.75g (substantially a weight ratio of 0.75% with respect to the entire quantity) of zirconium so that the alloy containing the proper amount of zirconium in accordance with the present invention is relatively free from liquation and therefore chemically stable as compared to the alloy without the addition of zirconium, although both alloys present the desired gold color.

In accordance with preferred embodiments of the present invention as above described, additional alloying amounts of such elements as nickel, indium, silicon, beryllium and lithium are added to the copper-zinc-zirconium alloy of the present invention in order to provide additional requirements as described below.

The addition of nickel is based on the requirement that all of the alloy be used as the material for crown repair of relatively small size, for example in the form of an inlay or a crown so that the same should be sufficiently rigid to be free from breakage, falling off due to deformation and collapse while simultaneously having sufficient flexibility or edge strength so that the edge portion is never chipped even when subjected to pressing or hammering operations and occlusion pressure. These functions correspond to the mechanical properties such as tensile strength, hardness and extensibility. The addition of the nickel is also advantageous in adding flexibility to the alloy and also to correct what would otherwise be an excessive copper tone. However, the addition of nickel in an amount of 1% or more is actually disadvantageous in that the resulting alloy presents a disagreeable discoloration to a bluish-violet tone while at the same time increasing the melting point required for working.

The addition of indium is effective for deacidification as well as for the improvement of the tensile strength and the extensibility. A particular advantage obtained by the addition of indium resides in the fact that in the presence of silicon, as described below, the brilliance of the alloy is improved, its melting point is lowered to a level which is preferable for working, its contraction during casting is reduced, its reproducibility faithful to the matrix is improved, and its discoloration resistance is also improved.

The addition of silicon, as above mentioned, is advantageous in that, in the presence of indium, the alloy obtains improved brilliance and finish. In this respect, the addition of lithium provides a similar effect, and in practice, a deacidifying effect upon the alloy is also obtained by the addition of one or both of these elements.

The addition of beryllium within a range of 0.01 to 0.02% provides a slight effect of deacidification and in an amount of approximately 0.1% contributes to improvement of the hardness and particularly of the castability of the alloy. In an amount greater than 1%, however, the addition of beryllium results in an excessively high hardness, a lower extensibility of the alloy and a melting point which is unfavorable with respect to working, so that the addition of more than 1% of beryllium is undesired.

Finally, chemical changes of an inlay which was made according to the alloy of embodiment 1 above and charged into the oral cavity of subjects is shown below in comparison with the prior art alloys used in restorative dentistry to show the clinical application of the gold color copper alloys of the present invention.

| Type of alloys | Number of cases | Discoloration in self-cleanable zone | Discoloration in unclean zone | Breakage |
| --- | --- | --- | --- | --- |
| 20K gold alloy | 172 | 18(10.0%) | 35(22.0%) | 0 |
| 14K gold alloy | 78 | 22(28.0%) | 53(72.0%) | 0 |
| Silver alloy | 216 | 46(21.0%) | 62(34.0%) | 10(6%) |
| Alloy of embodiment 1 | 139 | 13(9.0%) | 43(41.0%) | 0 |

While the invention has been described with respect to certain specific alloys, it is apparent that variations and modifications thereof can be made.

What is claimed is:

1. A gold color dental restoration formed of a copper alloy consisting essentially by weight of 48–52% of copper, 47–51% of zinc and 0.1–1.0% of zirconium, said dental restoration being chemically stable against discoloration and dissolution in the mouth in which it is applied.

2. The gold color dental restoration according to claim 1 and also containing nickel in an amount less than 1.2% by weight.

3. The gold color dental restoration according to claim 1 and also containing nickel in an amount of less than 1.2% by weight and indium in an amount of less than 1.0% by weight.

4. The gold color dental restoration according to claim 1 and also containing nickel in an amount of less than 1.2% by weight, indium in an amount of less than 1.0% by weight and silicon in an amount of less than 1.0% by weight.

5. The gold color dental restoration according to claim 1 and also containing nickel in an amount of less than 1.2% by weight, indium in an amount ofless than 1.0% by weight, silicon in an amount of less than 1.0% by weight and beryllium in an amount of less than 0.5% by weight.

6. The gold color dental restoration according to claim 1 and also containing nickel in an amount of less than 1.2% by weight, indium in an amount of less than 1.0% by weight, silicon in an amount of less than 1.0% by weight and lithium in an amount of less than 0.5% by weight.

7. The gold color dental restoration according to claim 5 and also containing lithium in an amount of less than 0.5% by weight.

* * * * *